(12) United States Patent
Hilpert

(10) Patent No.: US 6,316,633 B1
(45) Date of Patent: Nov. 13, 2001

(54) PROCESS FOR MANUFACTURE OF CHIRAL SUCCINIC ACID DERIVATIVES

(75) Inventor: Hans Hilpert, Reinach (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/699,912

(22) Filed: Oct. 30, 2000

Related U.S. Application Data

(62) Division of application No. 09/334,797, filed on Jun. 16, 1999, now Pat. No. 6,197,995, which is a division of application No. 09/153,103, filed on Sep. 15, 1998, now Pat. No. 5,952,507.

(51) Int. Cl.⁷ .................................................. C07D 263/26
(52) U.S. Cl. ............................................................. 548/230
(58) Field of Search ............................................. 548/230

(56) References Cited

U.S. PATENT DOCUMENTS 5,614,625  3/1997  Broadhurst et al. .

FOREIGN PATENT DOCUMENTS

| 029 909 | 8/1981 | (EP) . |
| 684 240 | 11/1995 | (EP) . |
| 816 341 | 1/1998 | (EP) . |

OTHER PUBLICATIONS

R. Beckett, et al. Syn. Lett. 137, Feb. 1993.
M. Schläpfer–Dähler, et al. Helv. Chim. Acta 75, 1251 (1992).
M. Sudharshan, P.G. Hultin, Synlett. 171 (1997).
Abstract corresponding to EP 816 341.
Abstract corresponding to EP 029 909.
Barrett, et al. J. Chem. Soc. 1935 1065–1969.

Primary Examiner—Patricia L. Morris
(74) Attorney, Agent, or Firm—George W. Johnston; Patrick S. Rocha-Tramaloni; Robert A. Silverman

(57) ABSTRACT

The present invention is concerned with a process for the manufacture of chiral succinic acid derivatives of formula (I)

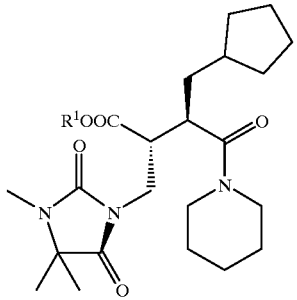

wherein $R^1$ is $(C_1–C_6)$ alkyl or benzyl, and the novel intermediates used therein.

2 Claims, No Drawings

PROCESS FOR MANUFACTURE OF CHIRAL SUCCINIC ACID DERIVATIVES

RELATION BACK UNDER 35 U.S.C. § 120

This is a divisional of copending application Ser. No. 09/334,797, filed on Jun. 16, 1999, now U.S. Pat. No. 6,197,995, which is a divisional of copending application Ser. No. 09/153,103 filed on Sep. 15,1998, now U.S. Pat. No. 5,952,507.

BACKGROUND OF THE INVENTION

Hydroxamic acid derivatives with tricyclic substitution, as shown in formula (X) below, are known for their pharmacological activity as cartilage protective agents and are particularly useful in the treatment and prevention of degenerative joint diseases such as atherosclerosis (U.S. Pat. No. 5,614,625, EP 684 240 A1).

Certain chiral succinic acid derivatives, as shown in formula (I) below, are valuable intermediates in the synthesis of the above compounds (EP 816 341 A1). Since these derivatives are chiral, it is important to develop a stereoselective reaction to most efficiently obtain the desired enantiomer. It is known that lithium bases such as LDA provide syn-selectivity (in ratios of up to 90:10) in reactions with succinic acid derivatives with an ester group and a free acid group (R. Becket et al., Synlett. 137, Feb. 1993). However sodium bases such as $NaN(TMS)_2$ are not specific, providing a 1:1 mixture of syn to anti addition products.

SUMMARY OF THE INVENTION

The present invention is concerned with a process for the manufacture of chiral succinic acid derivatives of formula (I)

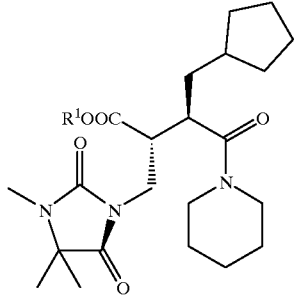

(I)

wherein $R^1$ is $(C_1-C_6)$alkyl or benzyl, which process comprises reacting a compound of formula (II)

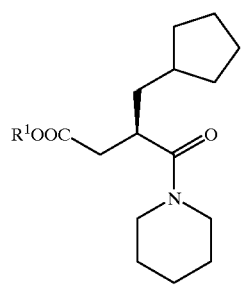

(II)

with a halohydantoin of formula (III)

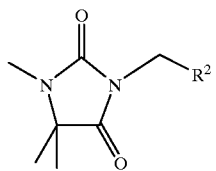

(III)

wherein $R^2$ is halogen, in the presence of a strong, enolate-forming potassium base.

By means of this reaction, the compound of formula (I) is obtained as the result of a selective anti-addition of the compounds of formulae (II) and (III). This is accomplished by use of a strong potassium base capable of forming an enolate. Surprisingly, in the case of an acid amide such strong potassium bases, such as $KN(TMS)_2$, $KNH_2$, KH or $C_1-C_6$ alkoxy potassium bases (for example potassium tert-butylate), achieve the necessary anti-selectivity required to efficiently produce the compound of formula (I).

DETAILED DESCRIPTION OF THE INVENTION

Accordingly, this invention is directed to a process for the manufacture of compounds of formula (I)

(I)

wherein $R^1$ signifies $(C_1-C_6)$alkyl or benzyl, which process comprises reacting a compound of formula (II)

(II)

with a compound of formula (III)

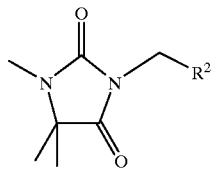
(III)

wherein R² is chlorine, bromine or iodine, in the presence of a strong potassium base capable of forming an enolate.

In a preferred process KN(TMS)₂ (potassium bis-trimethylsilylamide) is the potassium base. In another preferred process R¹ is tert-butyl. In another preferred process R² is bromine. In a particularly preferred process, KN(TMIS)₂ is the potassium base, R¹ is tert-butyl, and R² is bromine.

This invention is also directed to a process for the manufacture of compounds of formula (I)

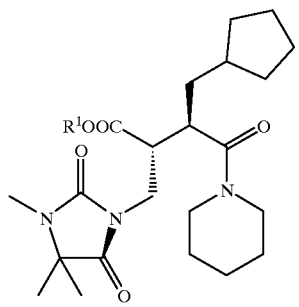
(I)

wherein R¹ signifies (C₁–C₆)alkyl or benzyl, which process comprises: a) reacting (S)-4-benzyl-2-oxazolidone with a compound of formula (IV)

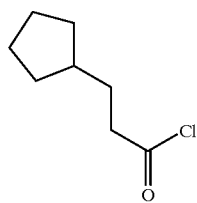
(IV)

to obtain (S)-3-(3cyclopentyl-1-oxopropyl)-4-(phenyl)-2-oxazolidinone (V); b) reacting (S)-3-(3-cyclopentyl-1-oxopropyl)-4-phenyl)-2-oxazolidinone (V) with a compound of formula (VI)

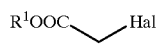
(VI)

wherein R¹ signifies (C₁–C₆)alkyl or benzyl and Hal signifies chlorine, bromine or iodine, to obtain a compound of formula (VII)

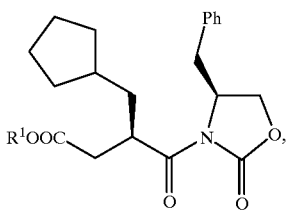
(VII)

c) cleaving (S)-4-benzyl-2-oxazolidinone from the compound of formula (VII) to obtain the compound of formula (VIII)

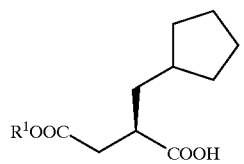
(VIII)

d) reacting the compound of formula (VIII) with piperidine to obtain a compound of formula (II)

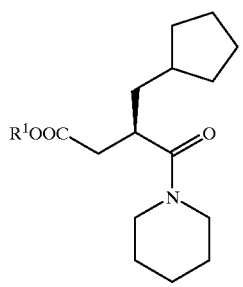
(II)

e) reacting the compound of formula (II) with a halohydantoin of formula (III)

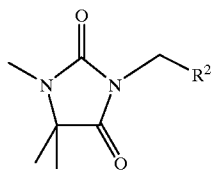
(III)

wherein R² is chlorine, bromine or iodine in the presence of a strong potassium base capable of forming an enolate, to obtain a compound of formula (I).

In a preferred such process KN(TMS)₂ is the potassium base. In another preferred process R¹ is tert-butyl. In another preferred process R² is bromine. In a particularly preferred process, KN(TMS)₂ is the potassium base, R¹ is tert-butyl, and R² is bromine. In another preferred such process the (S)-4-benzyl-2-oxazolidinone is cleaved by H₂O₂ and NaOH in a mixture of water and an alcohol.

Another process of this invention is a process for the manufacture of a compound of formula (X)

wherein a) in a compound of formula (I)

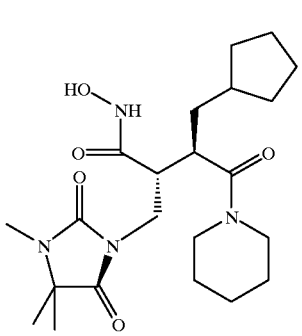

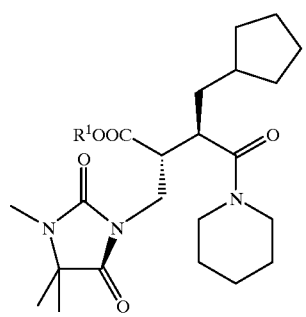

wherein $R^1$ has the significance given in formula 1, the $R^1$ is cleaved to obtain the compound of formula (IX)

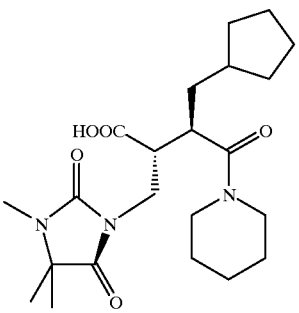

and b) hydroxylamine is added to the compound of formula (IX)

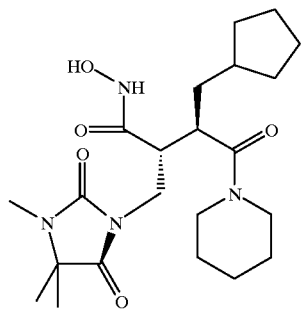

to obtain the compound of formula (X).

In a preferred such process $R^1$ is tert-butyl and is cleaved with a mineral acid in a carboxylic acid, especially where the mineral acid is HBr and the carboxylic acid is acetic acid. In another preferred process $R^1$ is $(C_1-C_6)$alkyl other than tert-butyl or a sterically hindered alkyl group and is cleaved with an alkali or alkaline earth metal hydroxide. In another preferred process $R^1$ is Bz and is cleaved hydrogenolytically. In yet another preferred process, the hydroxylamine is added: a) by means of trimethylsilyl-hydroxylamine or tetrahydropyranyl-hydroxylamine and cleavage of the trimethylsilyl or tetrahydropyranyl group, or b) by means of benzylhydroxylamine hydrochloride and hydrogenolytic cleavage of the benzyl group.

This invention is directed to another process for the manufacture of a compound of formula (X)

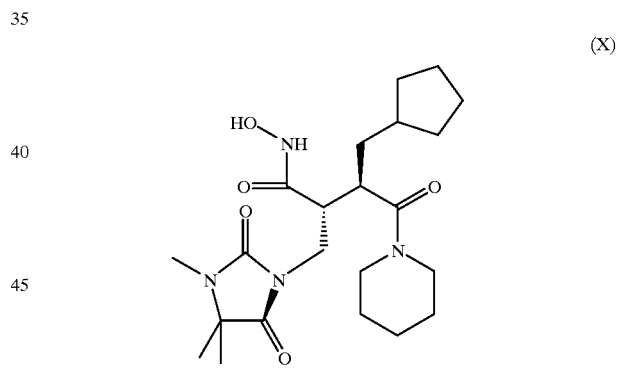

wherein a) a compound of formula (I)

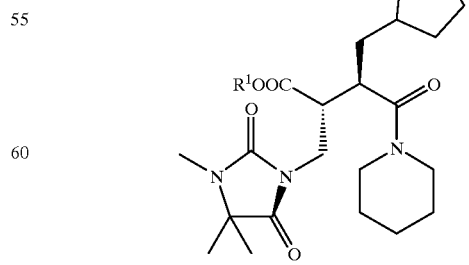

wherein R¹ is a straight chain $(C_1-C_6)$alkyl, is reacted with benzylhydroxylarine hydrochloride activated by alkylmagnesium halide and b) the benzyl group is hydrogenolytically cleaved off the resulting compound to obtain the compound of formula (X).

In a preferred such process R¹ is cleaved with an alkali or alkaline earth metal hydroxide.

This invention is also directed to compounds which are intermediates in the above-described processes.

These include compounds of formula (VII)

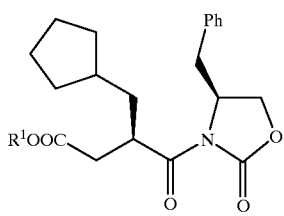

(VII)

wherein R¹ signifies $(C_1-C_6)$alkyl or benzyl, for example tert-butyl (R)-4-[(S)-4-benzyl-2-oxo-oxazolidon-3-yl]-3-cyclopentylmethyl-4-oxo-butanoate.

Also included are compounds of formula (VIII)

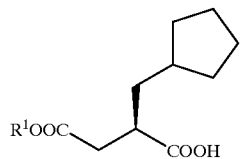

(VIII)

wherein R¹ signifies $(C_1-C_6)$alkyl or benzyl, for example (R)-2-cyclopentylmethyl-succinic acid-4-tert-butyl ester.

Also included are compounds of formula (II)

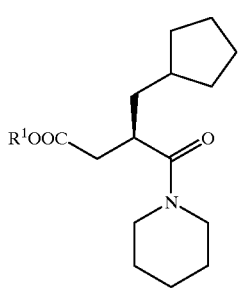

(II)

wherein R¹ signifies $(C_1-C_6)$alkyl or benzyl, for example tert-butyl (R)-3-cyclopentylmethyl-4-oxo-4-piperidin-1-yl-butanoate.

By halogen is meant chlorine, bromine and iodine. $(C_1-C_6)$Alkyl signifies a straight-chain or branched alkyl group with 1 to 6 C atoms, such as methyl, ethyl, propyl, butyl, pentyl, hexyl or isopropyl or tert-butyl. R¹ is preferably a $(C_1-C_4)$alkyl. $(C_1-C_6)$alkoxy means alkyl as defined above bonded to oxygen. By sterically hindered alkyl group is meant a branched alkyl group like iso-propyl, sec-butyl or, preferably, tert-butyl, which are not easily accessible to base cleavage. Strong potassium bases capable of forming an enolate are e.g., t-BuOK, KH, $KNH_2$ or, preferably, KN$(TMS)_2$. Bz stands for benzyl.

Compounds of formula (I) are described in EP 816 341 A1. Compounds of formula I are valuable intermediates in the synthesis of the pharmacologically active cartilage protecting compound (X) (U.S. Pat. No. 5,614,625, EP 684 240 A1). The compound of formula (X) has valuable pharmacological properties and can accordingly be used for the treatment and prevention of illnesses such as degenerative joint diseases, for example atherosclerosis.

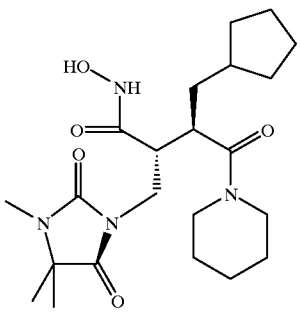

(X)

The alkylation of compounds of formula II with the halomethylhydantoin (III) is effected in a presence of a strong base in a solvent such as an ether, preferably THF, at a temperature of –100° to 22°, preferably –60° C.

The stereoselectivity of the newly formed stereocentre depends to a very large extent on the nature of the cation of the base. Lithium bases such as LDA, give rise to syn-selectivity (ratio up to 90:10), as has been described in the case of succinic acid derivatives having an ester group and a free acid group (R. Becket et al. in Synlett 137, Feb. 1993). On the other hand, sodium bases such as $NaN(TMS)_2$, are not specific (1:1 mixture).

Unexpectedly, it has now been found that in the case of an acid amide and the use of strong potassium bases capable of forming enolates, such as $KN(TMS)_2$ or $C_1-C_6$-alkoxy potassium bases (e.g. potassium tert-butylate) the anti-selectivity required for the manufacture of compounds of formula (I) is achieved. Preferably, $KN(TMS)_2$ is used in the manufacture of compounds of formula (I). With this an anti-selectivity in the ratio of 90:10 is achieved. The mixture of diastereomers can be separated by chromatography on silica gel with suitable solvents, such as, for example, hexane/ethyl acetate. The tert-butyl ester of formula (II) is preferably used as the ester.

The halohydantoin (D) used for the reaction with a compound (II) can be obtained by halomethylation of 1,5,5-trimethyl-hydantoin. Thus, 1,5,5-trimethyl-hydantoin is conveniently reacted with a hydrogen halide in acetic acid at a temperature between 20° and 100°, preferably at about 80°. The trimethylhydantoin can be obtained according to known methods (H. Heimgartner et al., Helv. Chim. Acta 75, 1251 (1992)). Halogen in this connection signifies chlorine, bromine or iodine. The halogen is preferably bromine.

In connection with the manufacture of compounds of formula (I) via compounds of formula (II), the present invention is also concerned with the manufacture of succinic acid derivatives of formula (I) by a process in which a) a compound of formula (IV)

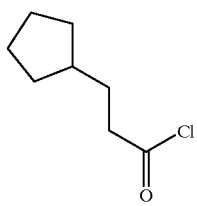

is reacted with (S)-4-benzyl-2-oxazolidinone to give (S)-3-(3-cyclopentyl-1-oxopropyl)-4-(phenylmethyl)-2-oxazolidinone (V), b) the product (V) obtained is reacted with a compound of formula (VI)

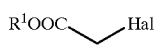

wherein $R^1$ signifies $(C_1$–$C_6)$alkyl or benzyl and Hal signifies halogen, to give a compound of formula (VII)

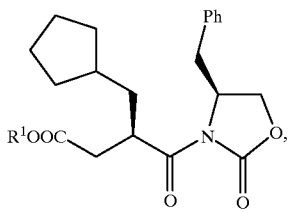

c) a compound of formula (VIII)

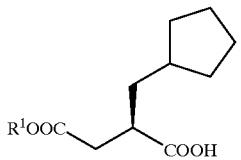

is obtained from compound (VII) with the cleavage of (S)-4-benzyl-2-oxazolidone, d) a compound of formula (II)

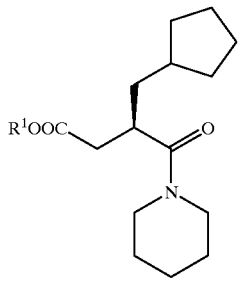

is obtained by reacting compound (VIII) with piperidine, and e) the thus-obtained compound of formula (II) is reacted with a halohydantoin of formula (III)

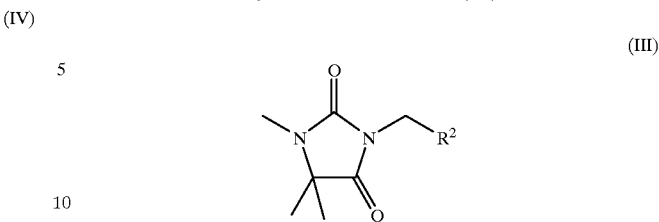

wherein $R^2$ is halogen.

For the performance of step e) reference is made to the foregoing description of the reaction of compounds of formula (II) with those of formula (III).

The acylation of (S)-4-benzyl-2-oxazolidinone (commercially available or producible according to M. Sudharshan, P. G. Hultin, Synlett, 171 (1997)) with cyclopentyl-propionyl chloride (IV) (Barret et al., J. Chemical Society 1065 (1935)) in accordance with step a) is effected according to methods known per se with a base, e.g. NaH, LDA, LiN(TMS)$_2$, or an alkyllithium compound, preferably BuLi, in a solvent such as an ether, preferably THF, at a temperature of –80° to 22°, preferably –45°. For the formation of the alkylated compounds (VII), the (S)-3-(3cyclopentyl-t-oxopropyl)-4-(phenylmethyl)-2-oxazolidinone which remains can be used in isolated form or, conveniently, in solution. The alkylation is effected with a halo-acetic acid ester, preferably tert-butyl bromoacetate in the presence of a base, e.g. LiN(TMS)$_2$ or preferably LDA in an aforementioned solvent, preferably THF, at –80° to 22°, preferably –45°. The product (VII) which is formed can be obtained from the reaction medium in high optical purity (de >99.9%) by crystallization following the addition of an alkane, preferably hexane, or by chromatography.

The halo-acetic acid esters of formula VI are commercially available or obtainable according to methods per se by the esterification of haloacetic acid derivatives.

The cleavage of the chiral auxiliary reagent from compounds of formula (VII) to give the acid (VIII) and (S)-4-benzyl-2-oxazolidinone in accordance with step c) can be effected according to known methods with hydrogen peroxide and LiOH in an ether such as tetrahydrofuran. The THF peroxide which thereby occurs represents a not inconsiderable safety risk. Surprisingly, it has now been found that the reaction proceeds quantitatively when the cheaper sodium hydroxide together with hydrogen peroxide in a mixture of water and an alcohol, preferably isopropanol, is used at a temperature of –10° to 22°, preferably 0°. The (S-)-4-benzyl-2-oxazolidinone which is thereby obtained crystallizes out almost quantitatively from the aqueous phase.

The amide formation of the acid (VIII) with piperidine in step d) can be effected according to known coupling methods such as via the acid chloride, via a mixed anhydride, via a mixed sulphonic acid anhydride or, preferably, via an active ester. In so doing there are used water-withdrawing agents such as carbodiimides, preferably dicyclohexylcarbodiimide in the presence of stoichiometric or catalytic amounts of active ester-forming alcohols, such as e.g. N-hydroxysuccinimide, N-hydroxybenzotriazole or preferably N-hydroxy-2-pyridone in a solvent such as a ketone, e.g. methyl ethyl ketone, or an ether, e.g. tert-butyl methyl ether, or a hydrocarbon, e.g. toluene, or a halogenated hydrocarbon, e.g. methylene chloride, or an ester, preferably isopropyl acetate, at a temperature of 0 to 80°, preferably 22°.

Compounds of formula (I) can be used in a process for the manufacture of a compound of formula (X)

c) the compound of formula (X)

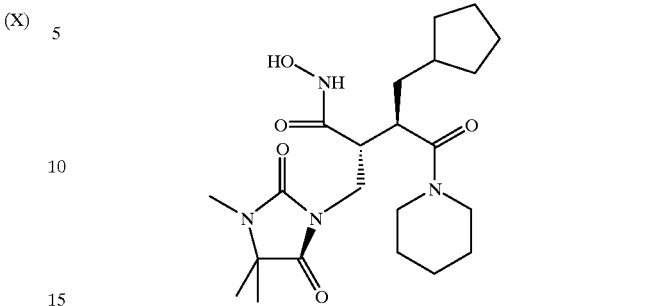

In this process a) a compound of formula (I)

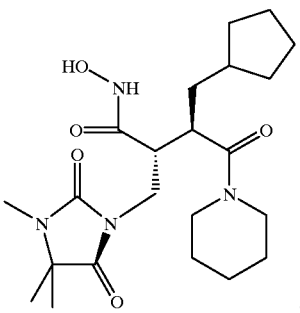

wherein R¹ signifies ($C_1$–$C_6$)alkyl or benzyl, is obtained in accordance with the foregoing description, b) the compound of formula (IX)

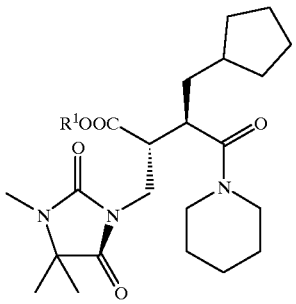

is subsequently produced by cleavage of the R¹ group, and is obtained by subsequent introduction of the hydroxylamine group into the compound of formula (IX), or d) a compound of formula (I) in which R¹ signifies straight-chain ($C_1$–$C_6$)alkyl is reacted with a benzylhydroxylamnine hydrochloride activated by means of an alkylmagnesium halide and subsequently the benzyl group is cleaved off hydrogenolytically, with compound (X) likewise being obtained.

The hydrolysis of an ester group in a compound of formula (I) in which R¹ signifies straight-chain or branched ($C_1$–$C_6$)alkyl, other than tert.butyl or a similar sterically hindered alkyl group, to the compound (IX) in accordance with section b) is effected in the presence of an alkali or alkaline earth metal hydroxide, such as barium, calcium, sodium or potassium hydroxide, preferably potassium hydroxide, in a solvent such as an alcohol, e.g. i-propanol, or water with an organic solvent, such as an ether, e.g. tert-butyl methyl ether, or preferably THF, at a temperature of 0 to 100°, preferably 30 to 50°.

The cleavage of the tert-butyl group or a similar sterically hindered alkyl group in a compound of formula (I) to give the compound (IX) in accordance with section b) is effected in the presence of a mineral acid, such as e.g. aqueous phosphoric or sulphuric acid, preferably hydrochloric acid or hydrobromic acid and an organic carboxylic acid, preferably acetic acid at a temperature of 0 to 100°, preferably 0–22°. The cleavage can also be carried out in a carboxylic acid ester or a mixture of carboxylic acid and carboxylic acid ester in place of a carboxylic acid. Suitable carboxylic acid esters are methyl, ethyl or isopropyl acetate, preferably ethyl acetate. HBr in acetic acid is the preferred cleavage method used. Furthermore, the cleavage by means of an acid can be effected in an otherwise suitable organic solvent. Methylene chloride or toluene is a suitable organic solvent.

The debenzylation of the compound (I) in which R¹ is equal to benzyl (Bz) in section b) to give compound (IX) is effected in an organic solvent using hydrogen in the presence of a metal catalyst. Suitable solvents are $C_1$–$C_6$-alcohols, preferably methanol or ethanol. As metal catalysts there can be used platinum or palladium, which are conveniently supported on a carrier material such as aluminium oxide, barium sulphate or charcoal. Palladium on charcoal or barium sulphate is a preferred catalyst. Temperature and pressure are not critical and can be varied in a wide range. Preferably, the hydrogenation is carried out at room temperature and 1–10 bar.

The introduction of the hydroxylamine group into compound (IX) in accordance with section c) can be effected by

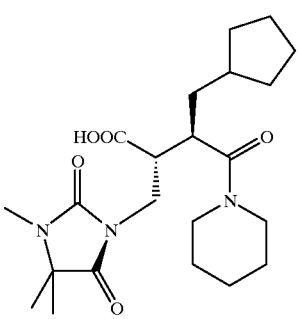

means of O-trimethylsilyl-hydroxylamine with activating agents known per se, such as carbodiimides, e.g. dicyclohexylcarbodiimide, or an isocyanide, e.g. tert-butyl isocyanide or, preferably, 2-morpholino-ethyl isocyanide, in the presence of stoichiometric or catalytic amounts of active ester-forming alcohols, such as e.g. N-hydroxysuccinimide, N-hydroxybenzotriazole or preferably N-hydroxy-2-pyridone, in a solvent, such as an ether, e.g. tert-butyl methyl ether, or a hydrocarbon, e.g. toluene, or a halogenated hydrocarbon, preferably methylene chloride, or an ester, preferably ethyl acetate, at a temperature of 0 to 80°, preferably 10 to 25°. Unexpectedly, it has been found that during the aqueous working-up the TMS protecting group is cleaved off smoothly and the desired product (X) can be obtained in high yield and purity without isolation of the TMS-protected intermediate.

The hydroxylamine group can be introduced using tetrahydropyranyl-hydroxylamine in an analogous maimer. The cleavage of the tetrahydropyranyl group is conveniently effected in an alcohol, such as methanol or ethanol, in the presence of a strong acid, such as a mineral acid, preferably HCl, or a sulphonic acid, preferably methanesulphonic acid or para-toluenesulphonic acid, at room temperature.

Alternatively, the hydroxylamine group can be introduced in c) using benzylhydroxylamine hydrochloride and an activating agent in a manner as described previously for the amide formation from the acid and piperidine. Especially preferred activating agents are carbodiimides, e.g. dicyclohexylcarbodiimide, or an isocyanide, e.g. tert-butyl isocyanide or, preferably, 2-morpholino-ethyl isocyanide, in the presence of stoichiometric or catalytic amounts of active ester-forming alcohols, such as e.g. N-hydroxysuccinimide, N-hydroxybenzotriazole or preferably N-hydroxy-2-pyridone. The use and production of such isocyanides is described in EP 29 909 B1.

The cleavage of the benzyl group is then effected by means of hydrogen and a catalyst as described previously for the debenzylation of a compound of formula (I) in which $R^1$ is equal to Bz.

Furthermore, in accordance with section d) the direct conversion of an ester in a compound of formula (I) in which $R^1$ signifies straight-chain ($C_1$–$C_6$)alkyl, preferably methyl, into the benzylhydroxamate can be effected by activation of the O-benzylhydroxylamine hydrochloride with an alkylmagnesium halide, preferably i-propylmagnesium chloride, in the presence of the ester (I) in a solvent, such as an ether, e.g. t-butyl methyl ether or, preferably, THF, at a temperature of −70° to 50°, preferably −20° to 0°.

The hydrogenolytic cleavage of the benzyl group to give compound (X) can then be effected in a similar manner to that previously described for the debenzylation of the compound (I) in which $R^1$ is equal to Bz.

In a preferred embodiment the manufacture of compound (X) from compounds of formula (I) is effected not via section d), but via section b) with $R^1$ equal to tert-butyl, followed by the subsequent reaction of compound (IX) with trimethylsilylhydroxylamine.

In accordance with the process steps set forth previously a compound of formula (X) can be obtained in a higher yield than according to the processes described in the state of the art.

The novel intermediates of formula (VII), (VIII) and (II) are also objects of the present invention. These are especially:
tert-butyl (R)-4-[(S)-4-benzyl-2-oxo-oxazolidon-3-yl]-3-cyclopentylmethyl-4-oxo-butanoate, (R)-2-cyclopentyhmethyl-succinic acid 4-tert-butyl ester and tert-butyl (R)-3-cyclopentylmethyl-4-oxo-4-piperidin-1-yl-butanoate.

EXAMPLES

EXAMPLE 1

A solution of 53.1 g of (S)-4-benzyl-2-oxazolidinone in 420 ml of tetrahydrofuran was treated at −45° with 197 ml of 1.6M butyllithium in hexane, a solution of 49.18 g of cyclopentylpropionyl chloride in 105 ml of tetrahydrofuran was subsequently added and the solution was stirred at −45° for 1 hr. The (S)-3-(3-cyclopentyl-1-oxopropyl)4-(phenylmethy)-2-oxazolidinone resulting as an intermediate was treated with 286 ml of a 1.1M lithium diisopropylamide solution in tetrahydrofuran at −45°, stirred for 1.5 hrs. and subsequently 64.38 g of tert-butyl bromoacetate in 60 ml of tetrahydrofuran were added. After 4 hrs. at −45° 600 ml of semi-saturated ammonium chloride solution were added, the THF phase was washed with semi-saturated sodium chloride solution, concentrated and crystallized by the addition of hexane, with 94.5 g (76%) of pure (de >99.9%) tert-butyl (R)-4-[(S)-4-benzyl-2-oxo-oxazolidin-3-yl]-3-cyclopentylmethyl-4-oxo-butanoate, m.p. 113–119°, being obtained. IR (KBr): 1768s, 1730s and 1695s (C=O).

EXAMPLE 2

A solution consisting of 36.7 g of 35% hydrogen peroxide and 8.31 g of sodium hydroxide in 78 ml of water was added at 0° to a suspension of 78.5 g of the oxazolidinone from Example 1 in 550 ml of isopropanol and the mixture was stirred at 22° for 1 hr. The solution was concentrated, made basic with sodium hydroxide solution and the precipitated (S)-4-benzyl-2-oxazolidinone was filtered off. Still present (S)-4-benzyl-2-oxazolidinone was extracted with methylene chloride, whereafter a total of 32.68 g (98%) of pure (S)-4benzyl-2-oxazolidinone, m.p. 86.5–88°, was recovered. The aqueous phase was adjusted to pH 3 with hydrochloric acid and extracted with isopropyl acetate. The organic extracts were washed, dried and evaporated, after which 47.79 g (99%) of enantiomerically pure (ee >99%) (R)-2-cyclopentyhnethyl-succinic acid 4tert-butyl ester were obtained as an oil. IR (film): 2700 m, br. (COOH), 1733s and 1710s (C =O).

EXAMPLE 3

A suspension of 34.48 g of the acid from Example 2 and 5.98 g of N-hydroxy-2-pyridone in 170 ml of isopropyl acetate was treated at 0° with 12.03 g of piperidine and subsequently with a solution of 30.53 g of dicyclohexylcarbodiimide in 92 ml of isopropyl acetate and stirred at 22° for 16 hrs. The suspension was treated with 82 g of 10% acetic acid in water and the mixture was stirred for 4 hrs. and filtered. The organic phase was washed with sodium carbonate and water, filtered and concentrated, after which 43.89 g (100%) of pure tert-butyl (R)-3cyclopentylmethyl-4oxo-4-piperidin-1-yl-butanoate (ee >99%), m.p. 38–40°, crystallizing from the oil, were obtained. IR (film): 1729s and 1641s (C=O).

EXAMPLE 4

A solution of 10.7 g of the ester from Example 3 in 50 ml of tetrahydrofuran was added dropwise at −60° to a solution of 8.76 g of potassium bis-trimethylsilylamide in 80 ml of tetrahydrofluran and the mixture was stirred at −60° for 30 min. Subsequently, a solution of 7.76 g of 3-bromomethyl-1,5,5-trimethylhydantoin in 40 ml of tetrahydrofliran was added at −60° and the mixture was stirred at −60° for 30 min. The reaction mixture was washed with semi-saturated sodium chloride solution and with dilute hydrochloric acid, dried, filtered and concentrated, there being obtained 15.11 g of a 9:1 mixture of 1-[2(R)-[1(R)-(tert-butoxycarbonyl)-2-(3,4,4-trimethyl-2,5-dioxo-1-imidazolidinyl)ethyl]-3cyclopentylpropionyl]piperidine and 1-[2(R)-[1(S)-(tert-butoxycarbonyl)-2-(3,4,4-trimethyl-2,5-dioxo-1-imidazolidinyl)ethyl]-3-cyclopentylpropionyl]piperidine (78% yield of pure anti-compound), which was used in the next step without further purification. The mixture can be separated by chromatography on silica gel with hexane/ethyl acetate (1:1).

EXAMPLE 5

A solution of 15.11 g of the 9:1 mixture from Example 4 in 15 ml of acetic acid was treated at 0° with 15 ml of 33% hydrogen bromide in acetic acid and stirred at 0° for 4 hrs. The solution was diluted with methylene chloride, washed with water and the organic phase was dried, filtered and evaporated. The residue was crystallized from 26 ml of tert-butyl methyl ether and 26 ml of hexane, after which 6.90 g (70%) of diastereomer-pure (de >98%) 1-[2(R)-[1(R)-carboxy-2-(3,4,4,-trimethyl-2,5-dioxo-1-imidazolidinyl)ethyl]-3-cyclopentylpropionyl]piperidine (IX), m.p. 111–114°, was obtained. IR (KBr): 1770m and 1715s (C=O).

EXAMPLE 6

A solution of 1.78 g of 1-[2(R)-[1(R)-(methoxycarbonyl)-2-(3,4,4-trimethyl-2,5-dioxo-1-imidazolidinyl)ethyl]-3-cyclopentylpropionyl]piperidine (European Patent Application published as EP 0 684 240 A1) in 3 ml of THF was treated with a solution of 0.69 g of KOH in 6.1 ml of water and stirred vigorously at 0° for 5 hrs. and at 40° for 10 hrs. The mixture was adjusted to pH 2 with dilute hydrochloric acid and treated with 8 ml of THF and 6 ml of saturated sodium chloride solution. The THF phase was washed with semi-saturated sodium chloride solution, dried and concentrated. The residue contained 1.86 g of up to about 95% pure 1-[2(R)-[1(R)-carboxy-2-(3,4,4-trimethyl-2,5-dioxo-1-imidazolidinyl)ethyl]-3-cyclopentylpropionyl]piperidine (IX). IR (KBr): 1769m and 1714s (C=O).

EXAMPLE 7

0.78 g of 2-morpholino-ethyl isocyanide was added to a suspension of 2.11 g of 1-[2(R)-[1(R)-carboxy-2-(3,4,4-trimethyl-2,5-dioxo-1-imidazolidinyl)ethyl]-3-cyclopentylpropionyl]piperidine (IX) from Example 5 or 6 and 0.61 g of N-hydroxy-2-pyridone in 21 ml of methylene chloride at 22° and the mixture was stirred for 3 hrs. The solution was treated with 0.58 g of O-trimethylsilyl-hydroxylamine and stirred for 2 hrs. The reaction mixture was washed with saturated $NaHCO_3$ solution and with water and evaporated. The residue was dissolved in 20 ml of tert-butyl methyl ether and 0.23 ml of water, stirred at 22° for 1½ hrs., the suspension was diluted with 10 ml of hexane, filtered and the residue was dried at 220/11 mbar, there being obtained 1.82 g (83%) of pure 1-[3-cyclopentyl-2(R)[1(R)-(hydroxycarbamoyl)-2-(3,4,4-trimethyl-2,5-dioxo-1-imidazolidinyl)ethyl]propionyl]piperidine (X), MS (EI): 436 (40%).

EXAMPLE 8

0.74 g of N-ethyhnorpholine, 0.60 g of N-hydroxybenzotriazole hydrate and 0.75 g of N-ethyl-N'-(3-dimethylaminopropyl)-carbodiimide were added at 0° in succession to a solution of 1.38 g of 1-[2(R)-[1(R)carboxy-2-(3,4,4-trimethyl-2,5-dioxo-1-imidazolidinyl)ethyl]-3-cyclopentylpropionyl]piperidine (IX) from Example 5 or 6 in 13 ml of methylene chloride and the mixture was stirred at 0° for 20 min. The reaction mixture was treated with 0.45 g of N-ethylmorpholine and 0.63 g of O-benzylhydroxylamme hydrochloride and then stirred at 0° for 30 min. and at 22° for 17 hrs. The solution was diluted with 13 ml of methylene chloride, washed with sodium bicarbonate solution and dilute hydrochloric acid, dried and concentrated. The residue was crystallized from ethyl acetate/hexane and the crystallizate was dried, there being obtained 1.26 g (73%) of pure 1-[2(R)-[1(R)-(benzyloxycarbamoyl)2-(3,4,4-trimethyl-2,5-dioxo-1-imidazolidinyl)ethyl]-3-cyclopentylpropionyl]piperidine, m.p. 138–140°.

Alternatively, 3.86 g of 2-morpholino-ethyl isocyanide were added to a suspension of 10.54 g of compound (IX) from Example 5 and 3.06 g of N-hydroxy-2-pyridone in 110 ml of methylene chloride at 22° and the mixture was stirred for 2 hrs. The solution was treated with 3.39 g of O-benzylhydroxylamine and stirred for 5 hrs. The reaction mixture was washed with dilute hydrochloric acid, $NaHCO_3$ solution and water, dried and concentrated. After recrystallization from methylene chloride/hexane the residue yielded 11.19 g (85%) of pure benzylhydroxamate, m.p. 140–142°.

EXAMPLE 9

A solution of 1.10 g of 1-[2(R)-[1(R)-(methoxycarbonyl)-2-(3,4,4-trimethyl-2,5-dioxo-1-imidazolidinyl)ethyl]-3-cyclopentylpropionyl]piperidine and 568 mg of O-benzylhydroxylamine hydrochloride in 7 ml of THF was treated at −20° with 3.5 ml of a 2M i-PrMgCl solution in THF and, after 1 hr. at −20°, again with 1.7 ml of the Grignard reagent. After a further 2½ hrs at −20° the mixture was treated with ammonium chloride solution and extracted with methylene chloride. The extracts were dried and concentrated. The residue was crystallized from tert-butyl methyl etherihexane and the crystallizate was dried, there being likewise obtained 1-[2(R)-[1(R)-(benzyloxycarbamoyl)-2-(3,4,4-trimethyl-2,5-dioxo-1-imidazolidinyl)ethyl]-3-cyclopentylpropionyl]piperidine, m.p. 135–137°.

EXAMPLE 10

For the debenzylation, a suspension of 5.5 g of 1-[2(R)-[1(R)-(benzyloxycarbamoyl)-2-(3,4,4-trimethyl-2,5-dioxo-1-imidazolidinyl)ethyl]-3propionyl]piperidine from Example 8 or 9 in 40 ml of ethanol and 1.7 g of Pd/C (5%) was hydrogenated at 22°/1 bar for 4 h. The suspension was filtered, the filtrate was concentrated completely and the residue was crystallized from water, there being obtained 3.9 g (85%) of pure 1-[3cyclopentyl-2(R)-[1(R)-(hydroxycarbamoyl)-2-(3,4,4-trimethyl-2,5-dioxo-1-imidazolidinyl)ethyl]propionyl]piperidine (X), MS (EI): 436 (40%).

What is claimed is:

1. Compounds of formula (VII)

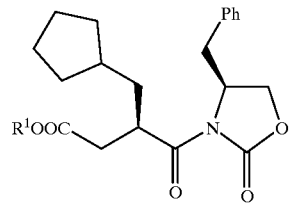

(VII)

wherein $R^1$ signifies $(C_1–C_6)$alkyl or benzyl.

2. A compound of claim 1 which is tert-butyl (R)-4-[(S)-4-benzyl-2-oxo-oxazolidon-3-yl]-3-cyclopentylmethyl-4-oxo-butanoate.

* * * * *